United States Patent
Nuss

(10) Patent No.: US 7,468,045 B2
(45) Date of Patent: Dec. 23, 2008

(54) TITANIUM MOLYBDENUM ALLOY GUIDEWIRE

(75) Inventor: Stephen Nuss, Minnetonka, MN (US)

(73) Assignee: Minnesota Medical Development, Inc., Plymouth, MN (US)

( * ) Notice: Subject to any disclaimer, the term of this patent is extended or adjusted under 35 U.S.C. 154(b) by 441 days.

(21) Appl. No.: 09/760,136

(22) Filed: Jan. 12, 2001

(65) Prior Publication Data

US 2006/0089568 A1     Apr. 27, 2006

(51) Int. Cl.
*A61B 5/00* (2006.01)
*A61M 25/00* (2006.01)

(52) U.S. Cl. .................................... 600/585
(58) Field of Classification Search ............... 600/433, 600/434, 585; 604/523, 524, 525, 528, 529, 604/530, 532
See application file for complete search history.

(56) References Cited

U.S. PATENT DOCUMENTS

| | | | | |
|---|---|---|---|---|
| 4,776,330 A * | 10/1988 | Chapman et al. | ............... | 606/64 |
| 4,817,600 A * | 4/1989 | Herms et al. | ................ | 606/198 |
| 4,984,581 A | 1/1991 | Stice | ........................ | 128/772 |
| 5,089,005 A | 2/1992 | Harada | ....................... | 606/194 |
| 5,429,501 A * | 7/1995 | Farzin-Nia et al. | ............ | 433/21 |
| 5,507,301 A | 4/1996 | Wasicek et al. | ............... | 128/772 |
| 5,551,443 A * | 9/1996 | Sepetka et al. | ............... | 600/585 |
| 5,673,707 A | 10/1997 | Chandrasekaran | ........... | 128/772 |
| 5,720,300 A * | 2/1998 | Fagan et al. | .................. | 600/585 |
| 5,772,609 A * | 6/1998 | Nguyen et al. | ............... | 600/585 |
| 5,797,857 A | 8/1998 | Obitsu | ......................... | 608/585 |
| 5,931,819 A | 8/1999 | Fariabi | ........................ | 604/281 |
| 5,984,679 A * | 11/1999 | Farzin-Nia et al. | .......... | 433/102 |
| 6,132,389 A * | 10/2000 | Cornish et al. | ............... | 600/585 |
| 6,402,859 B1 * | 6/2002 | Ishii et al. | .................... | 148/421 |
| 2003/0009095 A1 * | 1/2003 | Skarda | ......................... | 600/374 |
| 2003/0009215 A1 * | 1/2003 | Mayer | ........................ | 623/1.22 |

OTHER PUBLICATIONS http://www.dermnetnz.org/dna.nickel.allergy/info.html. Mar. 18, 2004.*

* cited by examiner

*Primary Examiner*—Max Hindenburg
*Assistant Examiner*—Jonathan M Foreman
(74) *Attorney, Agent, or Firm*—Thomas J. Nikolai; Nikolai & Mersereau, P.A.

(57) ABSTRACT

A guidewire for medical use such as in vascular and nonvascular systems. The guidewire made from a titanium molybdenum alloy wire with a composition of approximately 78% titanium 11.5% molybdenum 6% zirconium and 4.5% tin by weight such that it is softer than stainless steel guidewires and stiffer than NiTi alloy guidewires. The distal end of the guidewire is of a smaller diameter and softer than the proximal end and fitted with a coil for springiness such that the distal end will bend when encountering curves in the body passageways. The distal tip may be heat treated for a gradient of softness with the distal tip being the softest. The distal end may also be tapered to provide an additional gradient of softness. A distal tip on the distal end of the guidewire protects the wall of the passageway from being punctured as the guidewire travels through the passageway. The resulting guidewire has properties between those of stainless steel guidewires and NiTi alloy guidewires for better torsion and stiffness characteristics.

10 Claims, 2 Drawing Sheets

TITANIUM MOLYBDENUM ALLOY GUIDEWIRE

BACKGROUND OF THE INVENTION

1. Field of the Invention

This invention relates to the field of medical devices and more particularly to guidewires for use primarily in intra vascular procedures. Guidewires made with a titanium molybdenum alloy allow for a flexible and formable tip with reduced kinking, high torque, trackability and high column strength.

2. Description of the Related Art

A major requirement for guidewires and other guiding members, whether they are solid wire or tubular members, is that they have sufficient column strength to be pushed through a passageways in a patient such as the patient's vascular system with minimal kinking or binding. However, the distal section of the guidewire must be flexible enough to avoid damaging the blood vessel or other body lumen through which it is advanced. Efforts have been made to improve both the strength and flexibility of guidewires to make them more suitable for their intended uses, but strength for pushing and flexibility for turning without damaging vascular walls tend to be diametrically opposed to one another, in that an increase in one usually involves a decrease in the other. There has been a gradual decrease in the profiles or transverse dimensions of commercially available intravascular catheters and guidewires particularly for use in coronary arteries. However, concomitant with the decrease in profile has been a loss in pushability and kink resistance.

The distal portion of the guidewires frequently have a spring or coil around a tapered, thinner and therefore softer metal core. The thinner softer core may be too thin to engage the coil and may therefore allow the coil to kink when bent.

Guidewires have been made of many different materials. The most popular materials are stainless steel and NiTi alloys such as Nitinol.

Stainless steel guidewires tend to kink. They have good pushability but are not flexible enough to easily bend inside of the vascular system. Stainless steel has good torque qualities for rotating the guidewire but tends to bind when rotated since it does not readily flex. Once the guidewire is kinked, it must be discarded and replaced with a new guidewire.

NiTi guidewires tend to be too springy, especially when negotiating a tortuous path in vessels, they do not have good pushability because want to straighten out or return to their original shape. NiTi guidewires will readily get hung up when rotated while extending around a curved path. NiTi guidewires can not be torqued as readily as stainless steel because it is springy. NiTi guidewires tend to have good shape memory. The shape memory makes it difficult for a physician to shape the tip of the guidewire with his fingers for accessing difficult to reach portions of the patient's vascular system.

The guidewires need to have distal ends that are soft for bending and turning inside of the blood vessels as they are advanced and so they will not puncture the vessel walls.

The most popular guidewires are made out of stainless steel or NiTi alloys. Both of these materials have advantages and drawbacks. A different guidewire material is required to have the desirable qualities of both without as many drawbacks to enhance the performance of guidewires.

SUMMARY OF THE INVENTION

A titanium molybdenum alloy used to make guidewires for use in passages within a body has several advantages over NiTi and stainless steel guidewires. The titanium molybdenum alloy has properties of high springback, and flexability that is, in between the values of stainless steel and NiTi alloys which are the two most widely used metals used for making guidewires.

The titanium molybdenum alloy has moderate stiffness, about 42% of stainless steel and excellent torque transmission and formability. It is softer and more flexible than stainless steel for better bendability while negotiating though passageways in the body and less likely to puncture the walls of the passageways. The titanium molybdenum alloy is also easier to torque than stainless steel, which tends to bind when the guidewire is in nonlinear passageways. The titanium molybdenum alloy is stronger and has a better pushability than NiTi alloys and is easier to torque because it is less springy and will not bind against the walls of a vessel as much on a non linear path allowing easier rotation of the guidewire.

Titanium molybdenum alloys can be easily welded or soldered using standard manufacturing techniques, as opposed to NiTi alloys which are not easy to weld or solder.

The titanium molybdenum alloy can be tapered in steps at the distal end producing a softness gradient with the distal end the softest. This allows the distal tip to be more flexible and bend around curves without puncturing the tissue in the passageway. The titanium molybdenum alloy core is softer so it can be make thicker such that a coil around the core engages at a larger diameter and will not kink as it bends.

The titanium molybdenum alloy guidewire can be coated with a plastic such as Teflon® or a hydrophilic coating to make it slipperier.

The titanium molybdenum alloy is preferably a mixture of about 78% titanium 11.5% molybdenum 6% zirconium and 4.5% tin by weight.

OBJECTS OF THE INVENTION

It is an object of the invention to provide a guidewire with the right amount of stiffness to easily advance the guidewire.

It is an object of the invention to provide a guidewire with the right amount of softness to bend around curves in a passageway without puncturing the walls of the passageway.

It is an object of the invention to provide a guidewire with rotatability such that it can be torqued without binding up in a nonlinear passageway.

It is an object of the invention to provide a guidewire with a coil at the distal end of the guidewire which is less likely to kink when bent.

It is an object of the invention to provide a guidewire with a softness gradient at its distal end.

It is an object of the invention to provide a guidewire which steers better in the passageways of the patient.

It is an object of the invention to provide a guidewire which is easily weldable and solderable.

It is an object of the invention to provide a guidewire with an easily shaped tip.

It is an object of the invention to provide a guidewire with a radio opaque tip.

It is an object of the invention to provide a guidewire having a higher kink resistance than a stainless steel guidewire.

It is an object of the invention to provide a guidewire having less springiness than a NiTi alloy guidewire.

It is an object of the invention to provide a guidewire having a coating to make is easier to advance the guidewire though the vascular system of the patient.

Other objects, advantages and novel features of the present invention will become apparent from the following detailed description of the invention when considered in conjunction with the accompanying drawing.

DESCRIPTION OF THE PREFERRED EMBODIMENTS

Guidewires used in passageways within patients are used for a large number of medical procedures. Many of the procedures involve the use of the guide as a guidewire for inserting catheters and other devices in the vascular system of the patient. Guidewires have been made from stainless steel, which is stiff and does not readily bend around in the passageways of the patient. Guidewires are also frequently made using a NiTi alloy which is softer and springier than stainless steel and has a better memory but is not as stiff so that it does not have the pushability of stainless steel. Further NiTi alloy is not as easily bendable so that the distal tip can not be as readily shaped.

Figure 1:
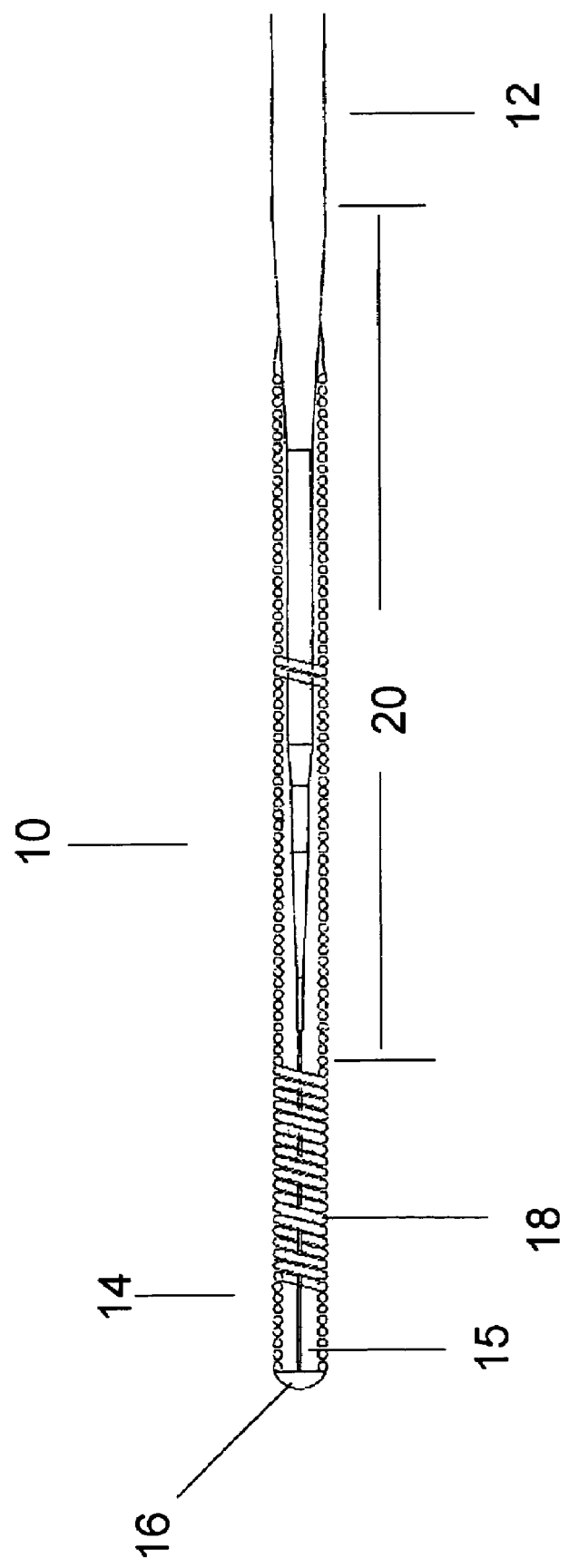
FIG. 1 is a side view of the guidewire.

A guidewire is shown in FIG. 1 having a titanium molybdenum alloy which has properties between that of stainless steel and NiTi alloys. The titanium molybdenum alloy is easier to use and has better torque, softness and pushability for use in the passageways of patients than guidewires made of other materials.

The guidewire in FIG. 1 is made from a titanium molybdenum alloy comprising about 78% titanium, 11.5% molybdenum 6% zirconium and 4.5% tin by weight. The stiffness is about 42% that of stainless steel.

Alternatively the guidewires can be made with a range of values for its alloys. The range of values is approximately 75-83% titanium, 8-14% molybdenum 4-8% zirconium and 2-6% tin by weight.

The titanium molybdenum alloy can be deflected more than 42% more than stainless steel with no permanent deformation and has a lower force deflection rate and a higher spring back and flexibility.

Comparing stainless steel to Nitinol, which is a NiTi alloy, stainless steel takes a set which is not a desirable quality for a guidewire and, Nitinol is too springy which is not a desirable quality for a guidewire. If a guidewire is too stiff it takes a set and will not easily bend. The stiffness however makes for good pushability allowing for the guidewire to be inserted into a passageway and allows the guidewire to be rotated at the distal end when turned at the proximal end. However if the guidewire does not bend easily and there is a nonlinear passageway that the guidewire must negotiate, the stiffness of the guidewire will form arches in the guidewire around curves and will not torque as easily since the entire guidewire will tend to push against the wall of the passage. If the guidewire is too springy and the guidewire is torqued the guidewire will bind in the curved portions in the passageways.

A guidewire made from a titanium molybdenum alloy is less springy than NiTi alloys but more springy than stainless steel. Titanium molybdenum alloys are stiffer than NiTi alloys and but not as stiff as stainless steel. Therefore titanium molybdenum alloys have desirable properties when used in guidewires.

Figure 2:
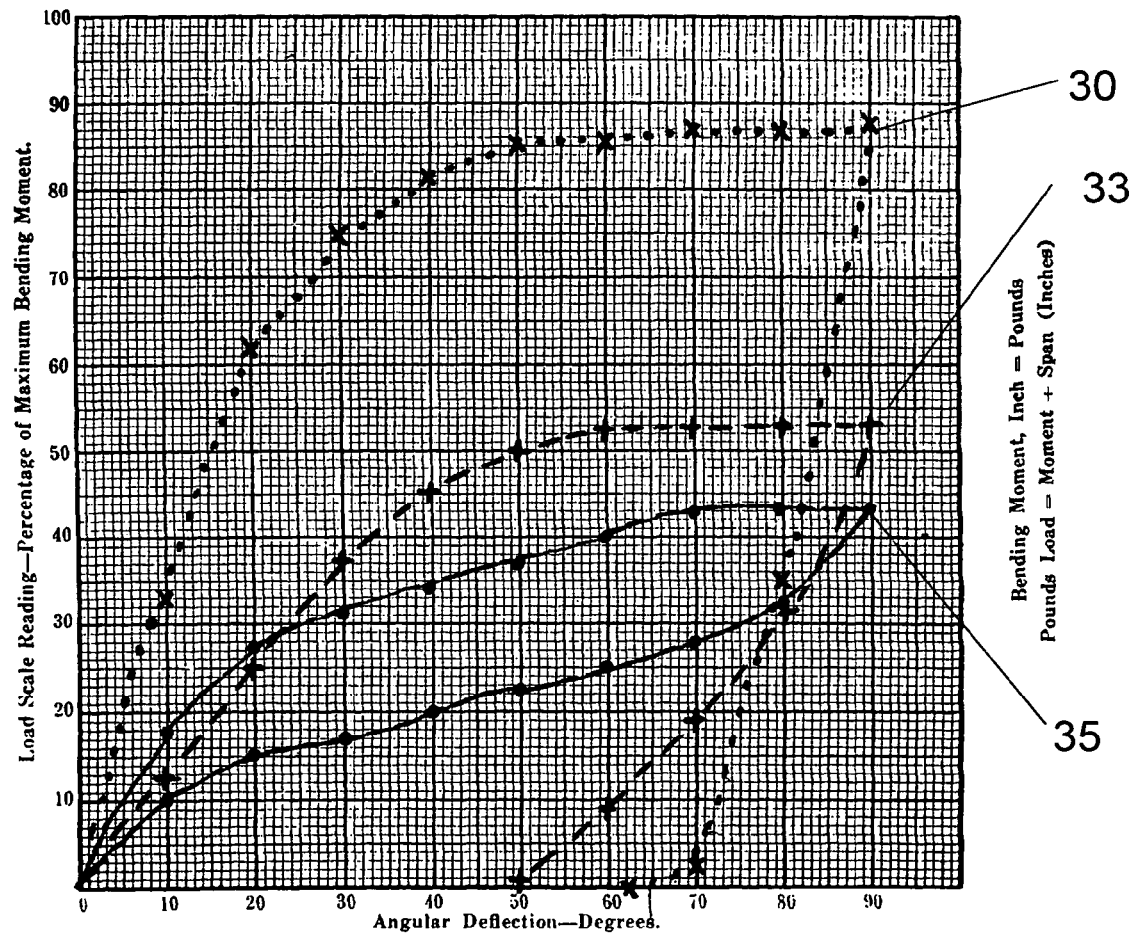
FIG. 2 is a graph comparing stress strain curves for NiTi alloy, stainless steel and TiMo alloy.

FIG. 2 shows the relative stress and strain curves comparing NiTi alloys, curve 35, stainless steel, curve 30 and titanium molybdenum alloy, curve 33 guidewires. The graph charts the percentage of maximum bending moment (inch=pounds) as related to the angular deflection (degrees). It shows the percentage that each wire returns to it's original shape after being bent to a given moment. As shown on the chart, when deflected, Nitinol returns to its shape, stainless steel returns to only about 5% of it's original shape and titanium molybdenum alloy such as Beta III alloy returns to about 50% of its original shape. Thus the titanium molybdenum alloy such as Beta III alloy exhibits springback properties between Nitinol and Stainless steel.

FIG. 1 shows a side view of a guidewire 10 having a proximal end 12 and a distal end 14. The distal end 14 has a smaller diameter than the proximal end 12 to make is softer and more easily bendable. It is desirable to have a softer distal end 14 such that the guidewire will bend and follow the curves of a blood vessel or other passageway that the guidewire is inserted into. The guidewire is provided with a rounded distal tip 16 at the tip of the distal end 15 to secure the coil 18 to the distal end 14 and to prevent the tip of the distal end 15 from penetrating tissue in the passageway as the guidewire is being inserted. The guidewire 10 is also provided with a coil 18 which can be made out of platinum, tungsten or similar radioopaque materials to act as a spring, allowing the thinned distal end 14 to bend and yet spring back into place after the guidewire is transported around a curve in the passageway.

In the past coils 18 would tend to kink and not return to their original shape if there was a large space between the inside diameter of coil 18 and the core of the distal end 14 of the guidewire 10. The titanium molybdenum alloy has a softness which allows it to have a larger diameter and still be soft enough at the distal end 14 such that the outside diameter of the distal end of the guidewire 10 engages the coil 18 on the inside diameter reducing the space therebetween and prevents the coil from kinking as the coil 18 and the distal end 14 bend. The coil 18 is wound around the core of the distal end 14 without spaces between the turns and in tight contact with core to prevent kinks from occurring when the guidewire is bent.

The titanium molybdenum alloy is made softer by tapering the distal end 14 to reduce the cross section of the guidewire. The tapering at the distal end 14 provides a gradient of softness with the tip of the distal end 15 being the softest. The gradient of softness helps the tip bend while keeping the remainder of the guidewire 10 straighter. The distal end 14 can have a tapered portion 20 which gradually changes the diameter of the guidewire material and provides for a gradient of softness.

Abrupt changes in the stiffness of the distal end of the guidewire causes kinking at stress points of the coil, when the distal end is bent. By having a larger number of tapered sections with small changes in the diameter the flexibility (bendability) of the guidewire can continually increase toward the distal end of the guidewire 14 without an abrupt change averting kinking.

The proximal end 12 of the guidewire is less flexible and is more uniform and can transmit torque and pushing force with high fidelity.

The titanium molybdenum alloy steers better than stainless steel guidewires or NiTi alloy guidewires because it is more flexible than stainless steel yet stiff enough to have torque and it stiffer than NiTi.

The distal tip 16 and coil 18 are attached to the titanium molybdenum alloy guidewire 10 by welding or soldering. The titanium molybdenum alloy is more easily welded or soldered than NiTi alloys.

The guidewire 10 can be coated with a plastic for making the guidewire slipperier. The guidewire can be coated with Teflon® or a similar material for a hydrophilic coating.

The proximal end 12 of the guidewire 10 can have a coating or surface making it easier to grasp for the doctor to more effectively use the guidewire.

The guidewire 10 can be made with lengths of preferably between 20 cm and 500 cm and between diameters of 0.005 inches and 0.040 inches with a coil length preferably of between 0.5 cm and 100 cm . . . .

The guidewire 10 can be made with lengths of preferably between 20 cm (7.87 inches) and 500 cm (196.85 inches) and between diameters of 0.127 cm (0.005 inches) and 1.02 cm (0.040 inches) with a coil length preferably of between 0.5 cm (0.197 inches) and 100 cm (39.37 inches).

Obviously, many modifications and variations of the present invention are possible in light of the above teachings. It is therefore to be understood that, within the scope of the appended claims, the invention may be practiced otherwise than as specifically described.

What is claimed is:

1. An intravascular guidewire adapted for insertion into the vascular system of a patient during the course of a catheterization procedure, comprising: a titanium molybdenum alloy wire having approximately 78% titanium, 11.5% molybdenum, 6% zirconium and 4.5% tin by weight, the wire having a diameter in a range of from 0.005 inch and 0.040 inch over a predetermined length dimension thereof, said wire having a proximal end portion and a distal end portion that is tapered to a lesser diameter than the diameter of the proximal end portion and that terminates in a rounded distal tip.

2. The guidewire as in claim 1 having,
the distal end portion with a helical coil attached, and where the coil touches a distal tip of the guidewire, the coil providing springiness proximate the distal tip inhibiting kinking of the coil.

3. The guidewire as in claim 1 having,
a rounded distal tip member on the end of the distal end portion of the wire to prevent the distal end of the wire from penetrating tissue in the wall of a body lumen upon passage of the guidewire through the body lumen.

4. The guidewire as in claim 1 wherein,
the wire has a lubricious polymer coating.

5. The guidewire as in claim 1 wherein,
the wire has a hydrophilic coating.

6. An intravascular guidewire adapted for insertion into the vascular system of a patient during the course of a catheterization procedure comprising a titanium molybdenum alloy wire having approximately between about 75% and about 83% titanium, between about 8% and about 14% molybdenum, between about 4% and about 8% zirconium and between about 2% and about 6% tin by weight, the wire having a diameter in a range of from 0.005 inch and 0.040 inch over a predetermined length dimension thereof, said wire having a proximal end portion and a distal end portion where the distal end portion is tapered to a lesser diameter than the diameter of the proximal end portion and terminates in a rounded distal tip.

7. The guidewire as in claim 6 having coil attached to a distal tip member such that the coil provides springiness at the distal tip portion to prevent kinking of the coil.

8. The guidewire as in claim 6 having,
a distal tip member on the distal end portion to prevent the distal end of the wire from penetrating tissue in the wall of said body passageway.

9. The guidewire as in claim 6 wherein,
the wire has a lubricious polymer coating thereon.

10. The guidewire as in claim 6 wherein,
the guidewire has a hydrophilic coating thereon.

* * * * *